(12) United States Patent
Provost et al.

(10) Patent No.: US 7,410,560 B2
(45) Date of Patent: Aug. 12, 2008

(54) DEVICE FOR STORAGE AND DELIVERY OF STANDARDS FOR GEL ELECTROPHORESIS

(75) Inventors: Roger Provost, Napa, CA (US); William Strong, El Cerrito, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 773 days.

(21) Appl. No.: 10/936,876

(22) Filed: Sep. 8, 2004

(65) Prior Publication Data

US 2005/0082170 A1  Apr. 21, 2005

Related U.S. Application Data

(60) Provisional application No. 60/502,424, filed on Sep. 11, 2003.

(51) Int. Cl.
*G01N 27/00* (2006.01)

(52) U.S. Cl. .................. 204/616; 204/606; 204/620

(58) Field of Classification Search ......... 204/456–470, 204/606–621
See application file for complete search history.

(56) References Cited

U.S. PATENT DOCUMENTS

| 5,587,062 | A | 12/1996 | Togawa et al. |
| 5,766,436 | A | 6/1998 | Alam |
| 6,156,182 | A | 12/2000 | Olech et al. |
| 2002/0027078 | A1 | 3/2002 | Anderson et al. |
| 2003/0196897 | A1 | 10/2003 | Alpenfels et al. |

*Primary Examiner*—Nam X Nguyen
*Assistant Examiner*—Jeffrey T Barton
(74) *Attorney, Agent, or Firm*—Townsend and Townsend and Crew LLP.; M. Henry Heines

(57) ABSTRACT

Gel plugs that can be stored in a sealed condition and delivered individually to an electrophoresis gel as standards for electrophoretic separations are retained in a cartridge that is cleanly breakable into individual sections, each section retaining a gel plug of predefined dimensions with standard solute mixtures embedded in the plug. The separation of any single section from the cartridge exposes opposing edges of the gel plug which permits the user to insert an implement into the section interior and to urge the plug out of the section and into a well of an electrophoresis gel. All manipulations are performed without any need for contact between the user and the gel.

7 Claims, 4 Drawing Sheets

DEVICE FOR STORAGE AND DELIVERY OF STANDARDS FOR GEL ELECTROPHORESIS

CROSS REFERENCE TO RELATED APPLICATION

This application claims benefit from U.S. Provisional Patent Application No. 60/502,424, filed Sep. 11, 2003, the contents of which are incorporated herein by reference in their entirety.

BACKGROUND OF THE INVENTION

1. Field of the Invention

This invention resides in the materials and equipment used in performing slab gel electrophoresis, and particularly in the use of standards for facilitating the analysis of solute mixtures separated by electrophoresis.

2. Description of the Prior Art

One of the most effective, convenient, economical, and commonly used methods of analyzing biochemical mixtures in the investigations done in clinical and research laboratories is slab gel electrophoresis, a technique which allows a series of samples to be analyzed simultaneously and the results detected on a qualitative basis by direct visual observation or on a quantitative basis by instrumentation. For these reasons, slab gel electrophoresis is widely used for analyzing protein mixtures in cell lysates and other biological samples, nucleic acid mixtures in DNA sequencing operations, and any of the wide variety of analyses of this sort that are commonly performed by biologists and biochemists. The two-dimensional shape of a slab gel makes it useful in horizontal pulsed-filed electrophoretic separations, such as the CHEF® system of Bio-Rad Laboratories, Inc., Hercules, Calif., USA, and in two-dimensional electrophoretic separations, where the slab gel serves as the second dimension of the separation, following a linear first dimension separation which is typically performed by isoelectric focusing in an immobilized pH gradient (IPG) strip gel. These are only examples; other applications of slab gel electrophoresis will be readily apparent to the skilled biochemist.

Analyses of protein or other solute mixtures by slab gel electrophoresis are helped considerably by the use of standards which may consist of mixtures of proteins, nucleic acid fragments, or whatever type of species is appropriate to the analysis, each mixture having a known composition for separation in the same gel alongside the samples to be analyzed, providing a comparison by which the components of the sample can be identified. These standards can assume a variety of forms. Paper standards for example are often used in when electrophoresis is performed in vertically oriented slab gels, i.e., when the gel is oriented such that the direction of migration is vertical, and gel plug standards are often used when the slab gel is oriented such that the direction of migration is horizontal. In each case, the standard is commonly loaded onto the slab gel in a position adjacent to the samples to be analyzed. When the gel is the second dimension of a two-dimensional separation, the first-dimension gel strip is placed along one edge of the gel and the standard is placed along the same edge at one end of the gel strip.

Among the various standards that are commercially available are precast gel plugs of Bio-Rad Laboratories, Inc. A set of plugs of agarose that contain DNA size markers embedded in the agarose are available from this supplier under the product name "DNA Size Marker, H. wingei" (Catalog No. 170-3667). To use this product, the user cuts a plug to the desired dimensions with a razor blade and then inserts the cut plug into the slab gel with a flat-bladed implement referred to as a "spatula." The use of these plugs thus involves individual handling of the plugs by the user which makes the procedure susceptible to user error and the possible loss of gel plug material. The same supplier also supplies plug kits that include plastic molds to enable one to cast one's own standard-containing agarose plugs in the laboratory. These kits are available under the product names "CHEF Mammalian Genomic DNA Plug Kit" (Catalog No. 170-3591), "CHEF Bacterial Genomic DNA Plug Kit" (Catalog No. 170-3592), and "CHEF Yeast Genomic DNA Plug Kit" (Catalog No. 170-3593). The casting of these plugs by the user adds to the tasks that the user must perform and, like the preformed plugs, requires the handling of individual pieces of gel material by the user.

Among the other standards of the prior art are those of New England Biolabs, Inc., Beverly, Mass., USA. The New England Biolabs standards consist of modified syringes filled with agarose with standards embedded in the agarose. These standards are sold under the product names "Yeast Chromosome PFG Marker" (Catalog No. NO345S), "Lambda Ladder PFG Marker" (Catalog no. NO340S), and "Low Range PFG Marker" (Catalog No. NO350S). To use these standards, the user depresses the syringe plunger to extrude the agarose containing the embedded standards, then slices off the desired amount for insertion in the gel. Similarly to the products described in the preceding paragraph, this entails the handling of a bare plug by the user.

These and other limitations of the prior art are addressed by the present invention.

SUMMARY OF THE INVENTION

This invention resides in a gel plug cartridge constructed in joined sections that can be manually separated for individual use, each section containing a single gel plug with predetermined amounts of the known proteins or other solutes that constitute the standard, allowing the user to load the plug directly onto an electrophoresis gel. Both the individual sections and the cartridge as a whole are encased in plastic or other suitable protective enclosure material, and thus both the separation of a section from the cartridge and the transfer of a gel plug from a separated section can be performed without any contact between the user's fingers and the gel plug material. Potential contamination of the gel and soiling the user's fingers are thus both avoided.

In preferred embodiments of the invention, the gel plugs in the cartridge are combined to form a continuous body of gel plug material extending throughout all sections of the cartridge, allowing all sections to be filled from the same solution of standard proteins, nucleic acids, or other solutes in gel-forming liquid so that all plugs will be identical in composition. In further preferred embodiments, the separation of any single section from the cartridge leaves an opening in the section at the site where the section was severed. This provides access to the gel plug and eliminates any need for the user to cut or otherwise open the section to remove the plug.

For convenience, the cartridge is supplied with an implement such as a trowel or blade that the user can use to push or otherwise draw the gel plug out of a section once the section is separated. Since preferred gel plugs are flat and rectangular in shape, the preferred implement is a flat, rectangular (spatula-shaped) device that is appropriately sized that it can be inserted into the separated section and once inserted, can push the entire gel plug out with a single motion. Such an implement can further be used to facilitate the positioning of the gel plug in a well in the electrophoresis gel. For further convenience, the implement can be joined to the cartridge as well, and preferably a separate implement is included for each cartridge so that one cartridge and one implement can be used for a single electrophoresis experiment and then discarded. These and other features, objects and advantages of the invention and its use will be apparent from the description that follows.

DETAILED DESCRIPTION OF THE INVENTION AND PREFERRED EMBODIMENTS

Figure 1:
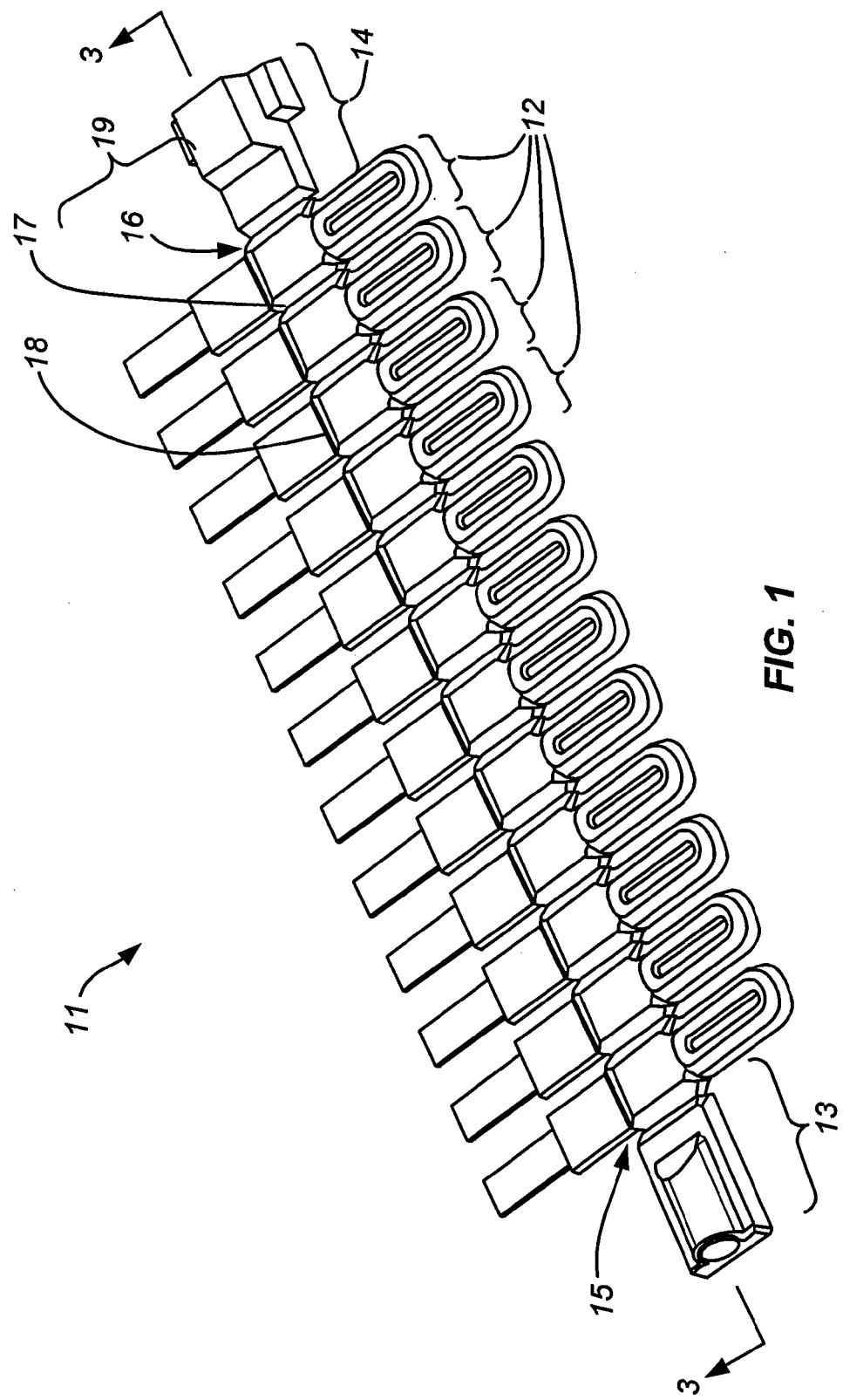
FIG. 1 is a perspective view of a cartridge that serves as one example of the present invention.

While the invention is susceptible to a wide range of configurations and embodiments, an understanding of the underlying concepts and principles of the invention and its novel aspects is best gained by a detailed review of a single embodiment. One such embodiment is depicted in the drawings and described below.

In the perspective view of FIG. 1, the cartridge 11 is shown to contain twelve plug sections 12 arranged linearly along the cartridge, and two end blocks 13, 14 with score lines, i.e. lines along which the cartridge can be separated manually by the user, at various locations. Two score lines 15, 16 are at locations defining the boundaries between the two end blocks 13, 14, respectively, and the plug sections. Eleven internal score lines 17, parallel to the end score lines 15, 16, define the boundaries between each pair of adjacent plug sections. Finally, twelve additional score lines 18, all aligned with each other, permit the separation of implements 19 ("spatulas") from the sections. As shown in succeeding drawings and explained further below, each section has an internal cavity to retain a gel plug, with connecting passages between the cavities of adjacent sections for flow communication so that all cavities can be filled from a common source in a single operation and the gels in all cavities can be cast simultaneously. The end blocks 13, 14 have entry and exit ports, respectively, communicating with the cavities and their connecting flow passages to permit the filling of the cartridge with a solution of standards while allowing air to escape, each port having a removable cap to seal the gel material inside the cartridge interior once filling is completed.

The first section to be used is one of the sections adjacent to a cartridge end. The section adjacent to the end block 13 to the left of the view in FIG. 1 serves as an example. To separate this section from the cartridge, the end block 13 is first broken off at the score line 15 between it and the section to be used, followed by breaking at the score line 17 along the opposing edge of the section, i.e., between the first and second sections. The breakage of these score lines exposes two opposing edges of the gel plug in the first section, and also exposes one edge of the gel plug in the second section. The latter can then be sealed or otherwise closed off with a temporary closure such as a removable film or tape until the second section is needed. The sections are used in sequence as needed, each successive section being taken from the end from which the last used section was removed.

Figure 2:
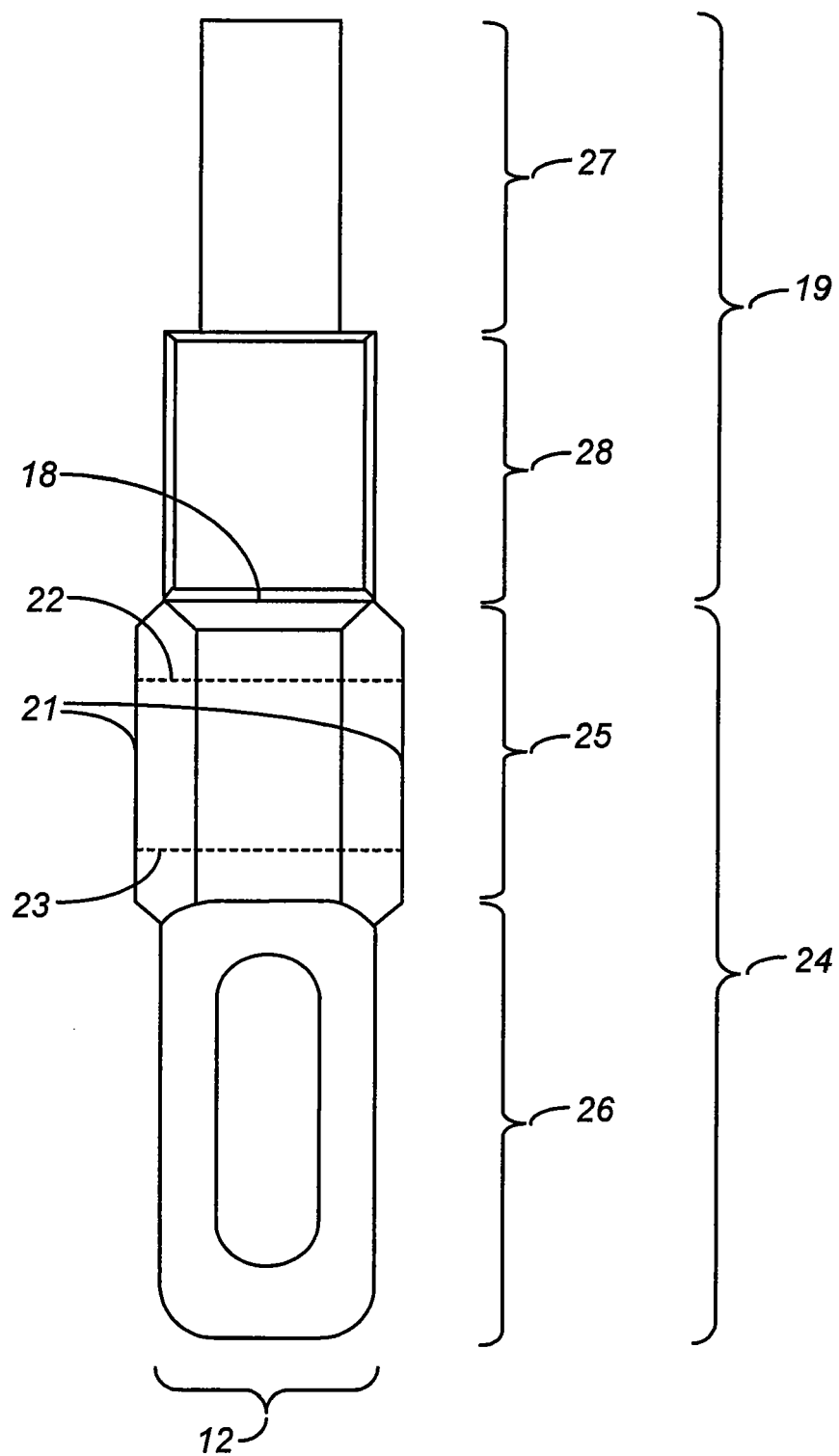
FIG. 2 is a plan view of one section of the cartridge of FIG. 1, separated from the remainder of the cartridge.

The enlarged view of FIG. 2 shows the features of an individual section 12 in greater detail after having been separated from its neighbors. Thus separated, the lateral extremities 21 of the section are defined by the locations where the score lines 17 were located. Narrow slits (not visible) at these locations, equal in thickness to the gel plug itself, provide access to the internal cavity of the section (and hence the gel plug), which is delineated in the drawing by dashed lines 22, 23. The section 12 once separated is further divided into two parts, the implement or spatula 19 and the gel plug holder 24, by breakage along the score line 18 that divides these parts. The gel plug holder 24 consists of a gel enclosure 25 and a handle 26 that can be grasped between the user's thumb and forefinger. The implement 19 includes a blade 27 and an implement handle 28 that can be grasped manually between the thumb and forefinger of the user's other hand. With the two parts now isolated and capable of being manipulated separately, the gel plug can be shoved out of the gel enclosure 25 by insertion of the blade 27 into the opening along one of the two edges 21 of the enclosure to force the plug out the opening along the other edge.

Figure 3:
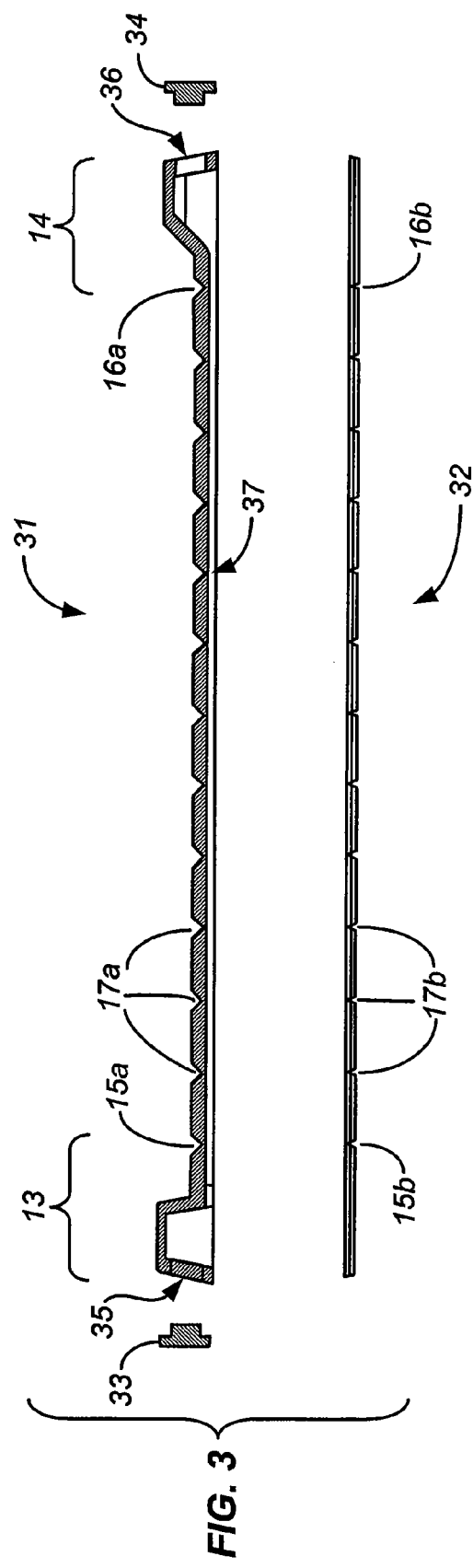
FIG. 3 is an exploded view of the cartridge of FIG. 1, illustrating one method of manufacture of the cartridge.

The interior of the cartridge can be seen in the exploded cross section shown in FIG. 3 which is taken along the line 3-3 of FIG. 1. For manufacturing purposes, this particular cartridge is made in two halves, i.e., an upper half 31 and a lower half 32 bonded together, either one, and preferably each, being a continuous molded piece. For gel loading purposes, the cartridge contains a left end plug 33 and a right end plug 34 sized to fit inside the ports 35, 36, respectively, in the two end blocks 13, 14 of the cartridge, thereby sealing the cartridge interior. The left end plug 33 and right end plug 34 are removable but can be bonded to the internal surfaces of the respective ports 35, 36 once the cavity is filled. In this view, the internal cavity 37, whose outline is indicated by the dashed lines 22, 23 in FIG. 2, is visible and extends the entire length of the cartridge at a constant height and width. The cavity thus has a uniform cross section with no dead volumes, thereby facilitating the complete filling of the cavity to achieve gel plugs that are uniform in size as well as composition. As shown in this cross section, the various transverse score lines 15, 16, 17 that define the divisions between the sections and the end blocks consist of score lines in the upper half 15a, 16a, 17a and opposing score lines in the lower half 15b, 16b, 17b. The separation of any two sections or segments of the cartridge along a score line is readily achieved by grasping the sections or segments on either side of the score line and bending at the score line to weaken the connection, followed in some cases by a twisting motion to complete the break.

Figure 4:
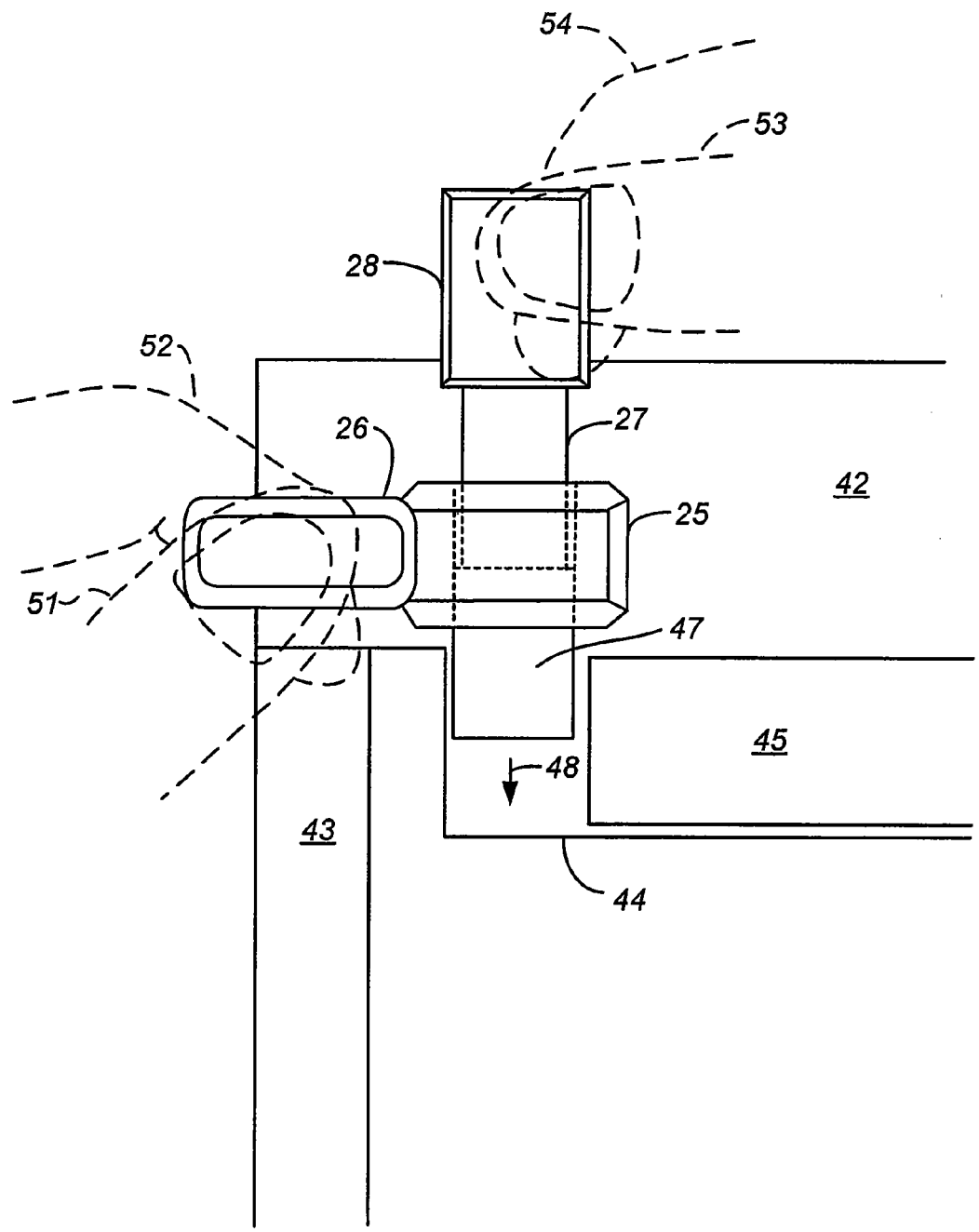
FIG. 4 is a plan view of an electrophoresis gel retained between transparent plates of unequal height, in the process of receiving a gel plug from a section of the cartridge of FIG. 1.

Use of a single section of the cartridge is shown in FIG. 4. An electrophoresis gel 41 resides between a pair of glass or plastic plates, which in this example are of unequal height. Of the two plates, only the rear plate 42, whose edge extends beyond that of the forward plate, is shown. Both plates extend above the gel, leaving a space above the gel for the samples to be loaded. In two-dimensional electrophoresis, the space is long enough to accommodate the IPG strip in which the first-dimension separation was performed. Spacers along the two lateral edges of the gel (only one spacer 43 being shown in this drawing) establish the gap width between the plates and hence the thickness of the gel.

The description of the second stage of a two-dimensional electrophoretic separation procedure illustrates the use of a gel plug cartridge in accordance with this invention. The slab gel is cast in the gap between the plates with an elongated well 44 formed along the top edge of the gel during the casting stage. An IPG strip 45 in which the first-dimension separation has been performed is placed in the well, and a standard gel plug 47 from the cartridge section is also placed in the well at one end of the IPG strip. The plug is transferred to that well from the cartridge section by the user who holds the gel holder 25 by its handle 26 between the thumb 51 and forefinger 52 of one hand and the implement blade 27 by its handle 28 between the thumb 53 and forefinger 54 of the other hand. The user places the gel holder 25 close to the entrance to the opening at the top of the well 44, inserts the blade 27 into the gel holder 25, and pushes the gel plug down into the well in the direction indicated by the arrow 48. Once the IPG strip and the gel plug are in position, a melted agarose (or other gel) solution is applied over the strip and plug, filling the remainder of the well 44 and then solidified to assure full electrical contact between both the strip and plug and the slab gel.

The cartridge can be manufactured from conventional materials of construction, including the plastics commonly used in laboratory equipment, and particularly those used in the gel molds and enclosures of the prior art. The choice of materials is well within the purview of those routinely skilled in the design, manufacture, and/or use of such equipment. Any plastic or other material that can be cleanly broken at score lines by manual pressure can be used. Plastic parts can be formed by conventional molding methods.

The foregoing is offered primarily for purposes of illustration. Variations, substitutions and modifications in the configurations, shapes and methods of manufacture and use of the cartridge that still embody the concepts and features that distinguish this invention from the prior art will be apparent to those skilled in the art and are intended to be included within the scope of this invention.

What is claimed is:

1. A gel plug cartridge for use as a source of standards in gel electrophoresis, said gel plug cartridge comprising a plurality of sections that are manually separable along predetermined separation lines, an internal cavity extending through all sections and filled with a gel in which is embedded a preselected mixture of solutes to be used as a standard, and, for any single section once separated from said cartridge, means for urging gel from said section out of said section and into a well of a slab gel.

2. The gel plug cartridge of claim 1 wherein said plurality of sections are arranged linearly along said cartridge.

3. The gel plug cartridge of claim 2 wherein said gel plug cartridge comprises a continuous molded piece with score lines therein separating said sections.

4. The gel plug cartridge of claim 2 wherein said gel plug cartridge comprises a continuous molded piece formed in upper and lower halves, each half containing score lines separating said sections.

5. The gel plug cartridge of claim 1 wherein said means for urging is a flat blade affixed to said section and manually separable therefrom along a score line.

6. The gel plug cartridge of claim 1 further comprising, for any single section, a handle capable of being grasped manually.

7. The gel plug cartridge of claim 1 further comprising ports at opposing ends of said internal cavity and end plugs sized to fit inside said ports and thereby seal said internal cavity.

* * * * *